(12) United States Patent
Moline et al.

(10) Patent No.: US 11,698,332 B2
(45) Date of Patent: Jul. 11, 2023

(54) DEVICES HAVING A SAMPLE DELIVERY COMPONENT

(71) Applicant: HEWLETT-PACKARD DEVELOPMENT COMPANY, L.P., Houston, TX (US)

(72) Inventors: Robert Moline, Corvallis, OR (US); Manish Giri, Corvallis, OR (US); Chantelle Domingue, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 571 days.

(21) Appl. No.: 15/748,393

(22) PCT Filed: Nov. 24, 2015

(86) PCT No.: PCT/US2015/062426
§ 371 (c)(1),
(2) Date: Jan. 29, 2018

(87) PCT Pub. No.: WO2017/091213
PCT Pub. Date: Jun. 1, 2017

(65) Prior Publication Data
US 2018/0356327 A1    Dec. 13, 2018

(51) Int. Cl.
*G01N 15/06* (2006.01)
*B01L 3/00* (2006.01)
(Continued)

(52) U.S. Cl.
CPC .... *G01N 15/0656* (2013.01); *B01L 3/502715* (2013.01); *C12Q 1/25* (2013.01);
(Continued)

(58) Field of Classification Search
CPC ......... G01N 15/0656; G01N 33/54366; G01N 33/48707; G01N 33/50; G01N 1/38;
(Continued)

(56) References Cited

U.S. PATENT DOCUMENTS 8,242,792 B2     8/2012  Drimusz et al.
8,329,437 B1 *  12/2012  Ayliffe ............... G01N 15/1056
                                                        422/68.1
(Continued)

FOREIGN PATENT DOCUMENTS

TW         200805025         1/2008
WO      WO-2007076549        7/2007

OTHER PUBLICATIONS

Grady et al (A Clinical Evaluation of Routine Blood Sampling Practices in Patients with Diabetes: Impact of Fingerstick Blood Volume and Pain, Journal of Diabetes Science and Technology, 8 pages, 2014, see attached document) (Year: 2014).*

(Continued)

*Primary Examiner* — Elizabeth A Robinson
*Assistant Examiner* — Jean Caraballo-Leon
(74) *Attorney, Agent, or Firm* — Foley & Lardner LLP

(57) ABSTRACT

Examples herein provide a device. The device includes a sample delivery component, which includes: a reagent chamber to contain at least one reagent; a sample chamber to contain a fluid sample; and a delivery channel extending from the reagent chamber and in fluid communication with the sample chamber and an output port, wherein the delivery channel is conducive mixing the at least one reagent and the fluid sample to form a mixture before the mixture reaches the output port and be discharged therefrom. The device includes a testing cassette detachable from the delivery component, which includes: an input port in fluid communication with a microfluidic reservoir, the input port to (Continued)

receive the discharged fluid sample from the output port; and a micro-fabricated integrated sensor in a microfluidic channel extending from the microfluidic reservoir.

20 Claims, 4 Drawing Sheets

(51) Int. Cl.
*C12Q 1/25* (2006.01)
*G01N 33/487* (2006.01)
*G01N 33/543* (2006.01)
*G01N 1/38* (2006.01)
*G01N 33/50* (2006.01)
*G01N 15/00* (2006.01)

(52) U.S. Cl.
CPC ......... *G01N 1/38* (2013.01); *G01N 33/48707* (2013.01); *G01N 33/50* (2013.01); *G01N 33/54366* (2013.01); *B01L 2200/027* (2013.01); *B01L 2200/16* (2013.01); *B01L 2300/0636* (2013.01); *B01L 2300/0825* (2013.01); *B01L 2300/0867* (2013.01); *B01L 2300/1827* (2013.01); *B01L 2400/0406* (2013.01); *B01L 2400/0442* (2013.01); *B01L 2400/0487* (2013.01); *G01N 2015/0065* (2013.01)

(58) Field of Classification Search
CPC .............. G01N 2015/0065; C12Q 1/25; B01L 3/502715; B01L 2400/0487; B01L 2400/0406; B01L 2400/0442; B01L 2300/1827; B01L 2300/0867; B01L 2300/0825; B01L 2300/0636; B01L 2200/16; B01L 2200/027
See application file for complete search history.

(56) References Cited

U.S. PATENT DOCUMENTS

| 2002/0173745 | A1* | 11/2002 | Santini, Jr. ............... A23L 2/52 604/67 |
| 2004/0179427 | A1* | 9/2004 | Yamazaki ........... B01F 13/0059 366/348 |
| 2007/0031283 | A1* | 2/2007 | Davis ................ A61B 5/14546 422/400 |
| 2009/0286327 | A1 | 11/2009 | Cho et al. |
| 2012/0122139 | A1 | 5/2012 | Park et al. |
| 2012/0301371 | A1 | 11/2012 | Augstein et al. |
| 2013/0041236 | A1* | 2/2013 | Pugia ................ A61B 10/0045 600/309 |
| 2013/0295588 | A1 | 11/2013 | Watkins et al. |
| 2014/0166483 | A1* | 6/2014 | Chow .................... B03C 5/005 204/451 |
| 2014/0170679 | A1 | 6/2014 | Aitchison et al. |
| 2014/0248621 | A1 | 9/2014 | Collins |
| 2014/0308661 | A1* | 10/2014 | Holmes ................. G01N 35/00 435/6.1 |
| 2015/0044696 | A1 | 2/2015 | Dothie et al. |
| 2015/0298119 | A1 | 10/2015 | Williams et al. |

OTHER PUBLICATIONS

Ottino et al. (Introduction: mixing in microfluidics, The Royal Society, 2004, see attached document), (Year: 2004).*

* cited by examiner

```
┌─────────────────────────────────────────────────────┐
│ Providing a fluid sample to a device, the device comprising: │
│     a sample delivery component, comprising:        │
│         a reagent chamber to contain at least one   │
│ reagent;                                            │
│         a sample chamber to contain the fluid sample; │
│ and                                                 │
│         a delivery channel extending from the reagent │
│ chamber and in fluid communication with the sample chamber │
│ and an output port, wherein the delivery channel is conducive │
│ to mixing the at least one reagent and the fluid sample to form │
│ a mixture before the mixture reaches the output port and be │
│ discharged therefrom; and                           │
│         a testing cassette detachable from the sample delivery │
│ component, comprising:                              │
│             a sample input port in fluid communication with a │
│ microfluidic reservoir, the input port to receive the discharged │
│ fluid sample from the output port; and              │
│             a micro-fabricated integrated sensor within a │
│ microfluidic channel extending from the microfluidic reservoir │
└─────────────────────────────────────────────────────┘    S401

│
                            ▼

┌─────────────────────────────────────────────────────┐
│ Performing an analysis of the fluid sample using at least the │
│ micro-fabricated integrated sensor                  │    S402
└─────────────────────────────────────────────────────┘
```

Fig. 4

DEVICES HAVING A SAMPLE DELIVERY COMPONENT

BACKGROUND

Various sensing devices are currently available for sensing different attributes of fluid, such as blood. In some cases, a microfluidic device is used to analyze an analyte.

BRIEF DESCRIPTION OF THE DRAWINGS

The drawings are provided to illustrate various examples of the subject matter described herein in this disclosure (hereinafter "herein" for short, unless explicitly stated otherwise) related to a device, particularly one having a sample delivery component, and are not intended to limit the scope of the subject matter. The drawings are not necessarily to scale.

FIG. 4 provides a flowchart showing the processes involved in a method described herein.

DETAILED DESCRIPTION

Figure 1:
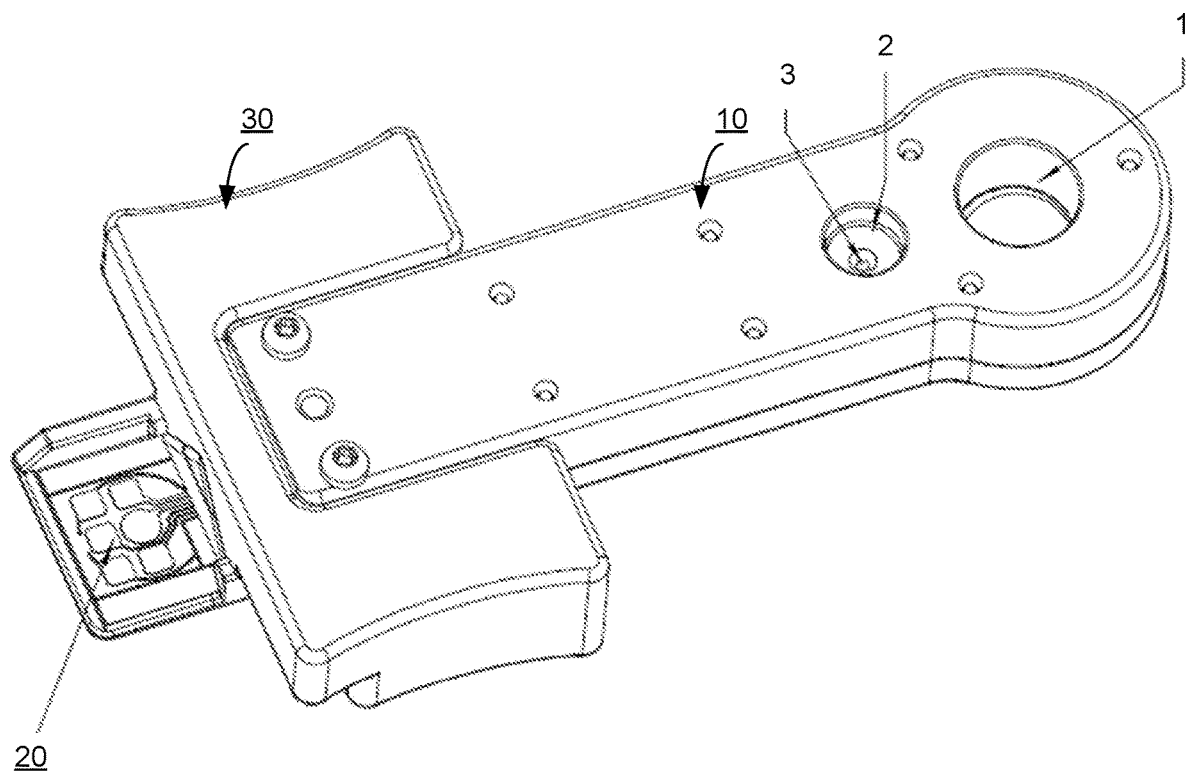
FIG. 1 provides a schematic showing a perspective view of an example device as described herein.

Standard methods for determining biological cell counts usually involve milliliter-scale blood samples collected by venipuncture in a doctor's office or laboratory. They are generally carried out using a flow cytometer or automated hematology analyzer. These instruments may be expensive, bulky, and are skill intensive to operate and maintain. Also, results may be delayed for hours or even days, which in turn delays diagnosis and treatment.

Biological fluids, such as blood, may be a complex and highly concentrated mixture of multiple cell types, proteins, and other components. Analysis by flow cytometry or automated hematology analyzers often involve sample dilution greater than 200 times (a ratio of sample to reagent of less than 1:200). As such, sample preparation methods used in these devices are often not easily scaled to work in low volume point-of-care settings.

In view of the aforementioned challenges related to biological fluid sample analysis, the Inventors have recognized and appreciated the advantages of a low-cost, portable, and easy-to-use diagnostics tool without compromising selectivity and accuracy. Following below are more detailed descriptions of various examples related to a device, particularly one having a sample delivery component. The various examples described herein may be implemented in any of numerous ways.

Provided in one aspect of the examples is a device, comprising: a sample delivery component, comprising: a reagent chamber to contain at least one reagent; a sample chamber to contain a fluid sample; and a delivery channel extending from the reagent chamber and in fluid communication with the sample chamber and an output port, wherein the delivery channel is conducive to mixing the at least one reagent and the fluid sample to form a mixture before the mixture reaches the output port and be discharged therefrom; and a testing cassette detachable from the delivery component, comprising: an input port in fluid communication with a microfluidic reservoir, the input port to receive the discharged fluid sample from the output port; and a micro-fabricated integrated sensor in a microfluidic channel extending from the microfluidic reservoir.

Provided in another aspect of the examples is a device, comprising: a sample delivery component, comprising: a reagent chamber to contain at least one reagent; a sample chamber to contain a fluid sample; a delivery channel extending from the reagent chamber and in fluid communication with the sample chamber and an output port, wherein the delivery channel is conducive to mixing the at least one reagent and the fluid sample to form a mixture before the mixture reaches the output port and be discharged therefrom; and an elastomeric layer to prevent the fluid sample from leaking out of the delivery channel; and a testing cassette detachable from the sample delivery component, comprising: a microfluidic channel; a micro-fabricated integrated sensor in the microfluidic channel; and a transport mechanism to pass the mixture in the microfluidic channel over a portion of the sensor for analysis.

Provided in another aspect of the examples is a method, comprising: providing a fluid sample to a device, the device comprising: a sample delivery component, comprising: a reagent chamber to contain at least one reagent; a sample chamber to contain the fluid sample; and a delivery channel extending from the reagent chamber and in fluid communication with the sample chamber and an output port, wherein the delivery channel is conducive to mixing the at least one reagent and the fluid sample to form a mixture before the mixture reaches the output port and be discharged therefrom; and a testing cassette detachable from the sample delivery component, comprising: an input port in fluid communication with a microfluidic reservoir, the input port to receive the discharged fluid sample from the output port; and a micro-fabricated integrated sensor within a microfluidic channel extending from the microfluidic reservoir; and performing an analysis of the fluid sample using at least the micro-fabricated integrated sensor.

To the extent applicable, the terms "first," "second," "third," etc. herein are merely employed to show the respective objects described by these terms as separate entities and are not meant to connote a sense of chronological order, unless stated explicitly otherwise herein.

The term "fluid" is meant to be understood broadly as any substance that continually deforms (flows) under an applied shear stress. In one example, a fluid includes an analyte (e.g., sample to be analyzed). In another example, a fluid includes a reagent or reactant. In another example, a fluid includes an analyte and a reagent or reactant. In another example, a fluid includes an analyte, a reagent or reactant, among others.

The term "pathogen" herein is meant to be understood as any substance that can produce a disease. In one example, the pathogen may be found in any fluid as described above.

The term "reagent" herein is meant to be understood as a substance or compound that is added to a system in order to bring about a chemical reaction, or added to see if a reaction occurs. A reactant is meant to be understood as a substance that is consumed in the course of a chemical reaction.

Figure 2:
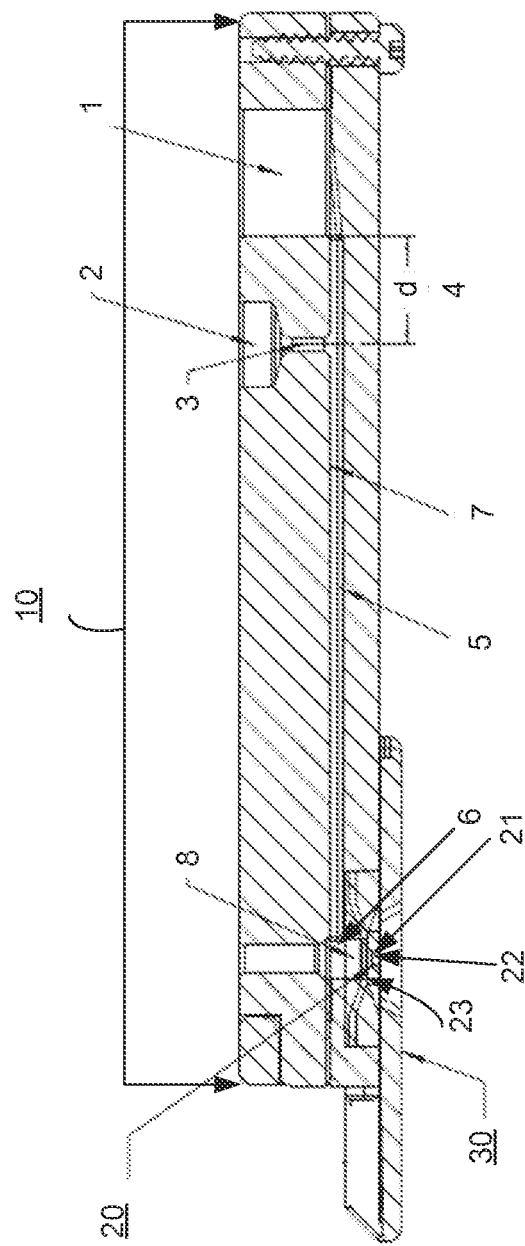
FIG. 2 provides a schematic showing a cross sectional view of an example device as described herein.
Figure 3:
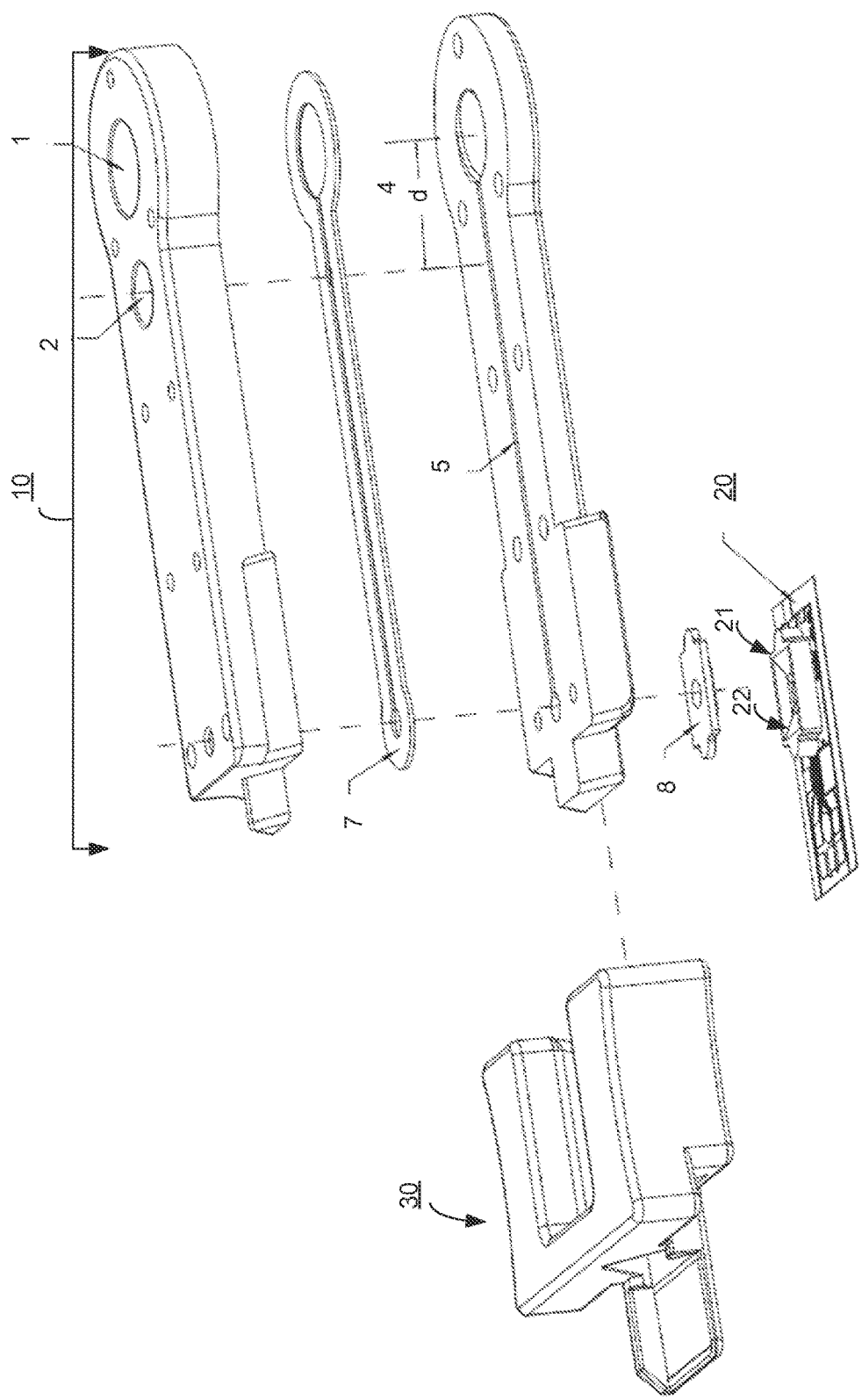
FIG. 3 provides a schematic showing an exploded isometric view of an example device as described herein.

The term "a number of" or similar language is meant to be understood broadly as any positive number including 1 to infinity, FIG. 1 shows a schematic diagram illustrating the components of an example device as described herein. FIG. 2 provides a schematic showing a cross sectional view of an example device as described herein. FIG. 3 provides a schematic showing an exploded isometric view of an example device as described herein. To facilitate illustration, the same components in the different figures are referred by the same reference numbers.

Sample Delivery Component

The device as shown in the figures may have a sample delivery component 10 and a testing cassette 20. The sample delivery component 10 may have any suitable number of sub-components. As shown in the figures, the sample delivery component 10 may comprise a reagent chamber 1, which may be employed to contain at least one reagent. The reagent need not be of a specific type or number and may be any suitable type and number depending on the application and the sample to be delivered. The reagent chamber may be pre-loaded with the at least one reagent, such that the reagent chamber comes with the at least one reagent therein in the package. In another example, the reagent is not pre-loaded with the reagent in the package, and at least one reagent is loaded therein only when needed. The sample delivery component 10 may also comprise a sample chamber 2, which may be employed to contain the sample to be delivered to the testing cassette for analysis. The sample may be a fluid sample. The sample may be a biological sample. The sample may be a biological fluid sample. A biological fluid sample may contain animal or human blood, animal or human urine, animal or human feces, animal or human mucus, animal or human saliva, yeast, or antigens, among others.

The sample delivery component 10 may have a delivery channel 5. As shown in the figures, the delivery channel may be extending from the reagent chamber 1 and in fluid communication with the sample chamber 2 and an output port 6. The delivery channel 5 may be conducive to mixing the at least one reagent and the fluid sample to form a mixture before the mixture reaches the output port 6 and be discharged from the output port. The delivery channel 5 may have any suitable geometry. For example, the width of the delivery channel 5 may be between about 0.1 mm and about 10 mm—e.g., between about 0.2 mm and about 5 mm, between about 0.5 mm and about 1 mm, etc. Other values are also possible. In one example, the width is about 0.32 mm. The depth of the delivery channel 5 may be between about 0.1 mm and about 10 mm—e.g., between about 0.2 mm and about 5 mm, between about 0.5 mm and about 1 mm, etc. Other values are also possible. In one example, the depth is about 0.32 mm. The length of the delivery channel 5 may be between about 5 mm and about 50 mm—e.g., between about 10 mm and about 40 mm, between about 20 mm and about 30 mm, etc. Other values are also possible. In one example, the length is about 37 mm.

The reagent chamber 1 and the sample chamber 2 may have any suitable configuration, including shape and size. The reagent chamber 1 may be bigger than, smaller than, or of the same size as the sample chamber 2. As shown in the figures, the sample chamber 2 and reagent chamber may be separated by a distance (d) ("4"), and the distance may be of any suitable value to provide a desired predetermined mixing ratio between the reagent(s) and the sample. The distance 4 herein may refer to the distance between one edge of the reagent chamber 1 to the center of the sample chamber 2 as shown in FIG. 2.

Also, the distance 4 may be any suitable value sufficient to achieve at the output port 6 (described later) a predetermined amount of mixing of the at least one reagent and the fluid sample. In one example, the distance 4 is between about 1 mm and about 15 mm—e.g., between about 2 mm and about 10 mm, between about 4 mm and about 8 mm. Other values are also possible. In one example, the distance 4 is about 5 mm. The predetermined amount of mixing may refer to any level of mixing in the reagent-sample mixture, ranging from 0 to 100%, with 0% referring to the reagent and the sample completely not mixed and 100% completely, homogeneously mixed. It is noted that the positions of the reagent chamber and the sample chamber as shown in the figures may be switched such that the sample chamber, and not the reagent chamber, is located at an end of the device.

In one example, the reagent chamber 1 may be cylindrical. The cylindrical chamber may have any suitable diameter and depth to achieve the configuration described above. For example, the diameter of the reagent chamber may be between about 1 mm and about 30 mm—e.g., between about 5 mm and about 25 mm, between about 10 mm and about 20 mm, etc. Other values are also possible. In one example, the diameter of the reagent chamber is about 6 mm. The depth of the reagent chamber may be between about 0.1 mm and about 15 mm—e.g., between about 0.5 mm and about 10 mm, between about 1 mm and about 5 mm, etc. Other values are also possible. In one example, the depth of the reagent chamber is about 3.6 mm.

In one example, the sample chamber 2 may be cylindrical. The cylindrical chamber may have any suitable diameter and depth to achieve the configuration described above. For example, the diameter of the reagent chamber may be between about 1 mm and about 20 mm—e.g., between about 2 mm and about 15 mm, between about 5 mm and about 10 mm, etc. Other values are also possible. In one example, the diameter of the reagent chamber is about 4 mm. The depth of the sample chamber may be between about 0.1 mm and about 10 mm—e.g., between about 0.5 mm and about 5 mm, between about 1 mm and about 3 mm, etc. Other values are also possible. In one example, the depth of the reagent chamber is about 1.6 mm.

The reagent chamber 1, the sample chamber 2, and the delivery channel 5 may each have a geometry such that at the output port 6 the fluid sample and the at least one reagent are mixed at a predetermined volume ratio. In one example, at the output port 6 the fluid sample and the at least one reagent are mixed at a volume ratio of greater than or equal to about 1:200 (sample:reagent(s))—e.g., greater than or equal to about 1:150, about 1:100, about 1:80, about 1:60, about 1:40, about 1:20, about 1:10, about 1:5, or higher. In one example, the ratio is about 1:9. In at least some examples, this ratio is much higher than some of the pre-existing blood diagnostic testing (e.g., 3-part white blood cell ("WBC") with % Diff), which involves a ratio of 1:1000 or lower—e.g., 1:10000 or lower.

As shown in FIG. 2, in some examples, the sample delivery component 10 may further comprise a sample feed channel 3. The sample feed channel 3 may be in fluid connection between the sample chamber 2 and the delivery channel 5. The sample feed channel 3 may have any suitable configuration, including shape and size. For example, the sample feed channel 3 may be cylindrical. In one example, the diameter of the sample feed channel may be between about 0.1 mm and about 1 mm—e.g., between about 0.2 mm and about 0.5 mm, etc. Other values are also possible. In one example, the diameter of the sample feed channel is about 0.2 mm. The depth of the sample feed channel may be between about 0.1 mm and about 10 mm—e.g., between about 0.5 mm and about 5 mm, between about 1 mm and about 3 mm, etc. Other values are also possible. In one example, the depth of the sample feed channel is about 2 mm.

As shown in FIG. 2, in some examples the sample delivery component 10 may comprise an elastomeric layer 7. As shown in FIG. 3, the elastomeric layer 7 may be located surrounding the edges of the delivery channel 5. The elastomeric layer 7 may be employed to prevent the fluid sample from leaking out of the delivery channel 5. It is noted that while an elastomeric layer 7 is present in some of the examples described herein, such a layer need not be always be present. The elastomeric layer 7 may comprise any suitable material. For examples, the elastomeric layer 7 mat comprise Aflas® (available from Seals Eastern Inc, USA), ethylene propylene diene terpolymer (EPDM), nitrile rubber ("Burna-N"), fluorinated ethylene propylene ("FEP"), fluorosilicone, perfluoroelastomer (e.g., Kalrez® available from DuPont, USA), neoprene, polytetrafluoroethylene ("PTFE"), polyurethane, silicone, stainless steel, fluoropolymer elastomer (e.g., Viton®, available from DuPont, USA), etc.

In some examples, the reagent may be resident in the sample delivery component, such as in the reagent chamber prior to use. In this example, the user need only obtain and load a fresh blood sample, initiate the test, and read the results.

In some examples, the reagent and/or sample port volumes may be scaled to process a range of blood samples from about 1 μL to about 50 μL. The delivery channel dimensions and path may be modified to provide control over the mixing behavior and lysis incubation time to optimize sample quality at the time it reaches the microchip sensor of the testing cassette.

In some examples, the sample delivery component may be modified to accommodate multiple reagents and/or treatment pathways to enable more complex cytology analyses as well as immunology, molecular diagnostics, and infectious disease applications, among others.

In some examples, the sample delivery component may be modified to accommodate multiplexed testing (e.g. a 3-part WBC with % Diff. plus blood glucose, blood gasses, and immunology testing) using a single cassette and blood sample.

In some examples, the sample delivery component may include a waste collection vessel to capture treated and analyzed fluid. It may also include a blood sample overflow containment system to enhance user safety and reduce the risk of exposure to biohazardous materials. The collection vessel may be present as a part of the sample delivery component, or may be a part of the testing cassette, as described further below, or both.

The sample delivery component may be manufactured using any suitable manufacturing techniques. In some examples, the sample delivery component are manufactured using three-dimensional ("3-D") rapid prototyping techniques, injection molding, or other high precision, high-throughput manufacturing methods. It may be assembled with an adhesive and/or epoxy layer with or without screws to maintain a leak-free seal. In some other examples, the sample delivery component are manufactured using, ultrasonic welding, laser welding, lost wax molding, printed Si injection molding, etc.

Testing Cassette

Referring to FIGS. 1-3, the device described herein may have a testing cassette 20. The testing cassette 20 may be supported by a cassette support 30. The sample testing cassette 20 may have any suitable number of sub-components. The testing cassette 20 may comprise a microfluidic device. As shown in the figures, the testing cassette 20 may comprise an input port 21. The input port may be in fluid communication with a microfluidic reservoir (inside input port but not shown in the figures herein). The testing cassette 20 may also comprise a micro-fabricated integrated sensor 22 in a microfluidic channel (not shown) extending from the microfluidic reservoir.

The testing cassette 20 may be detachable from the delivery component. The test cassette 20 may be fitted to be compatible with the sample delivery component 10 such that the sample-reagent mixture discharged from the output port 6 may be received into the input port 21 of the testing cassette 20, such as without spillage. As shown in FIGS. 2 and 3, to facilitate the transfer of the fluid sample-reagent mixture (and to prevent leakage or spillage), in some instances an elastomeric seal 8 may be placed between the output port 6 of the delivery component 10 and the input port 21 of the testing cassette 20. In one example, the elastomeric seal may be a "negative" of the assembly of the input port 21 of the testing cassette 20. The elastomeric seal 8 may comprise any suitable material, such as any of those described for the elastomeric layer 7. The materials of the elastomeric seal 8 and the elastomeric layer 7 may be the same as or different from each other.

The microfluidic device, including the sensor, microfluidic channel, reservoir, etc. described above, may be used to help detect pathogens in the human body and diagnose an illness in a patient. A microfluidic device such as a microfluidic diagnostic chip ("MDC") may be a micro-fabricated integrated sensor 22 to receive a fluid including an analyte and analyze it for purposes of attempting to diagnose a disease in a patient, immunology analysis, and molecular diagnosis. For the sake of facilitating the discussion herein, an MDC here encompasses the micro-fabricated integrated sensor. Based on the result of the analysis, appropriate treatment may be applied to the subject (that provides the sample) in need thereof. The device described herein may be a part of a handheld portable device, such as a diagnostic device.

The microfluidic diagnostic chip described herein may include a functionalizable enzymatic sensor defined in a microfluidic channel in the microfluidic diagnostic chip. The functionalizable enzymatic sensor may include a binding surface to bind to an analyte (e.g. a biomarker such as an antibody) thereto. For example, fluid may be passed over the functionalizable binding surface using a number of microfluidic pumps to identify the analyte (e.g. biomarker) within the fluid. The identification of the analyte (e.g. biomarker) occurs when the analyte binds to, for example, an antibody on the binding surface. The binding surface may, for example, have a coating.

The microfluidic device in the testing cassette 20 may include a number of microfluidic channels including at least one sensor and a number of pumps to pump a fluid though the number of microfluidic channels wherein presence of the fluid on the sensor detects changes in the chemical characteristics of the fluid.

As explained above, the MDC 22 is part of the cassette 20. The cassette 20 may further include an electronic device interface electrically coupled to the MDC. The interface may allow the MDC to receive instructions and power from an external source such as a computing device. In one example, the MDC is the part of the cassette that receives a fluid including an analyte while the cassette and electronic device interface provide the physical body to house the MDC and the power and logic to operate the MDC respectively.

The cassette may serve as a housing into which the MDC and electronic device interface are housed and protected from contamination and damage. The cassette may also serve as a structure onto which a user may apply pressure in order to connect the electronic device interface to an electronic device, for example directly to a computing device or to a connector that can be attached to a computing device.

The electronic device interface may include any number of electrical contact points that may interface with an input/output port of an electronic device. In one example, the electronic device interface is a universal serial bus ("USB") interface capable of electrically coupling to a USB port in an electronic device. In other examples, the electrical contact points of the electronic device interface may fit into a PCI bus, a PCIE bus, a SAS bus, and a SATA bus, among others. In one example, the electronic device interface may include electrical contact points that interface with a specialized port in a specialized computing device.

The MDC may include a feed tray, or input port 21, into which a fluid including an analyte is placed. The feed tray directs the fluid into a fluidic slot of the MDC. During operation, the fluid is placed in the feed tray and passed into the fluidic slot. When the fluid is in the fluidic slot the MDC receives electrical power from an electrical device using the electronic device interface). As will be described below, the MDC may further include an antibody binding surface to be functionalized by an antibody. In one example, the antibody binding surface may be made of gold. In other examples, the antibody binding surface may be made of platinum, tantalum, silicon carbide, or silicon nitride, among others.

The MDC may further include a number of sensors located in a number of microfluidic channels defined in the MDC. The sensors may be micro-fabricated sensors. In one example, the sensor comprise an impedance-based microchip. The impedance sensors may be capable of measuring an impedance value of a fluid sample including an analyte as the fluid is passed over the sensor. In one example, these sensors may measure the impedance of the fluid over time. In another example, the sensors may measure the impedance of the fluid at any time, for any number of intervals, and over any length of time based on the analysis to be completed. In one example where a microfluidic pump is used to pump the fluid through the MDC, the sensors may measure the impedance of the fluid while the pump is not pumping.

In some examples, the device may further comprise a transport mechanism to move the fluid sample through the delivery channel 5. The transport mechanism may be in the sample delivery component, the testing cassette, or both. The mechanism may achieve this by at least one of a capillary pump, a thermal inkjet pump, and a pneumatic pump. In one example, the mechanism may employ kinetic energy.

In one example, the testing cassette may further comprise a transport mechanism 23 (as shown in FIG. 2) to transport or pass the sample-reagent mixture in the microfluidic channel over a portion of the sensor for analysis. For example, the cassette may include a number of resistors that serve as both microfluidic heaters and microfluidic pumps depending on the amount and/or the duration of the voltage applied to the resistor. The MDC may further include a bore that serves as a hole through which an amount of fluid in the MDC is ejected out of a microfluidic channel defined in the MDC. During operation of the MDC, a number of fluids may be introduced into a fluidic slot. The fluid may then flow, using a number of inlets, into a number of microfluidic channels. The flow of the fluid into these microfluidic channels is initially accomplished using capillary action and subsequently through the use of a resistor as a microfluidic pump (pump resistor). In some examples, the fluid may be mixed, reacted with another fluid, heated, pumped, and recirculated through the fluidic slot and microfluidic channels, discharged from the MDC, or combinations thereof.

The resistors may be thin film resistors. The thin film resistor may comprise tantalum or tantalum aluminum, platinum, gold, silicon carbide, silicon nitride, tungsten, or combinations thereof. In one example, the thickness of the resistor may be approximately 500 angstroms to 5000 angstroms. The resistor may be encapsulated with a passive film which is then encapsulated with a cavitation film. In one example, the passive film may comprise SiC or SiN and may be approximately 500-2000 angstroms thick. In another example, the cavitation film comprises tantalum or platinum and may be approximately 500-2000 angstroms thick.

In some examples, the testing cassette 20 may comprise a discharge reservoir (not shown). A discharge reservoir may comprise a cavity or chamber within a body arranged to receive fluid discharged from the MDC. In one example, the discharge reservoir has a minimum volume of 10 μL. Discharge reservoir contains fluid that has been passed through chip and that has been processed or tested. In one example, the discharge reservoir extends below microfluidic chip on an opposite side of microfluidic chip as sample input port such that microfluidic chip is sandwiched between sample input port and discharge reservoir. Discharge reservoir receives processed or tested fluid such that the same fluid is not tested multiple times. In one example, the discharge reservoir is completely contained within body and is inaccessible (but through the destruction of body such as by cutting, drilling or other permanent structures are breaking of body), locking the processed or tested fluid within body for storage or subsequent sanitary disposal along with disposal of cassette. In another example, the discharge reservoir is accessible through a door or septum, allowing processed or tested fluid to be withdrawn from reservoir further analysis of the tested fluid, for storage of the tested fluid in a separate container or for emptying of reservoir to facilitate continued use of cassette.

The testing cassette 20 may comprise additional sub-components. For example, the testing cassette 20 may comprise a membrane across a mouth of the sample input port sealing the mixture of the at least one reagent and fluid sample in the sample input port 21. The testing cassette may also comprise a removable packaging completely enclosing a body of the testing cassette body. Other additional suitable sub-components may be employed.

Analysis

Also, the technology described herein may be implemented as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

FIG. 4 provides a flowchart illustrating such an example. As shown in the figure, the method may comprise providing a fluid sample to a device (S401). The device may be any of those described herein. For example, the device may comprise a sample delivery component and a testing cassette detachable from the sample delivery component. The sample delivery component and the testing cassette may be any of those described herein. For example, the sample delivery component may comprise a reagent chamber to contain at least one reagent; a sample chamber to contain the fluid sample; and a delivery channel extending from the reagent chamber and in fluid communication with the sample chamber and an output port. The delivery channel may be conducive to mixing the at least one reagent and the fluid sample to form a mixture before the mixture reaches the output port and be discharged therefrom.

The testing cassette may be any of those described herein. For example, the testing cassette may comprise an input port in fluid communication with a microfluidic reservoir, the input port to receive the discharged fluid sample from the output port. The testing cassette may also comprise a micro-fabricated integrated sensor within a microfluidic channel extending from the microfluidic reservoir.

As shown in FIG. 4, the method may further comprise performing an analysis of the fluid sample using at least the micro-fabricated integrated sensor (S402). The analysis may refer to any type of analysis that may translate the results measured by the testing cassette into meaningful data. The analysis may involve using algorithm and at least one processor to perform any number of calculations and/or comparison. In some examples, the analysis result may be employed to further provide treatment to the subject (from which the sample is obtained) in need thereof.

Non-Limiting Working Example

Introduction

The example described herein provides a fluid delivery system ("FDS") for "just-in-time" automated preparation and delivery of human whole blood for a 3-part WBC with % Diff. performed by impedance analysis in a microfluidics-based point-of-care blood diagnostics device. The FDS (a) stores sample treatment reagents in sterile conditions and at ideal volumes; (b) accepts up to 20 µL human whole blood obtained by venipuncture or finger stick; (c) facilitates precise mixing of reagents with blood sample at ideal ratio(s); (d) safely contains the blood sample and reagents to minimize user exposure to biohazardous materials; (e) interfaces seamlessly with the a microchip and tablet platform; and (f) is disposable in normal biohazard sharps containers. In this example, the FDS is intended for use in preparing a human whole blood sample in vitro for a 3-part WBC with % Diff. with low dilution in a continuous flow process for analysis by impedance sensing. The FDS in this example is a medical device that performs automated cell counts, particularly those that function by impedance sensing, are microfluidics-based, and use microliter volumes of whole human blood in a point-of-care setting.

The leukocyte (white blood cell) population comprises 3 main subgroups including lymphocytes, monocytes, and granulocytes. A 3-part BC provides an absolute count of cells of each main subgroup. The percent differential (i.e., the ratio of each cell type with respect to the total count) is calculated from the absolute count data. Together, the absolute count and percent differential are important indicators of patient health. Counts and/or ratios outside the normal range may indicate a variety of disease conditions.

Fully automated blood sample preparation and analysis offered by microfluidics "lab-on-chip" technology of the microchip platform has the potential to benefit healthcare. By placing robust blood diagnostics tools in the hands of healthcare providers at the point-of-care, diagnosis time and costs can be reduced, enhancing patient care. The device described herein makes possible automated blood sample preparation for a 3-part WBC with % Diff. using microliter scale blood volumes obtained by finger stick.

The fluid delivery system is compatible with a reagent to chemically lyse erythrocytes in a microliter-scale sample of human whole blood in vitro within seconds of exposure. The system delivers the sample to the impedance sensing zone of the microchip at the precise moment when the leukocyte population is most readily analyzed. Blood samples can be obtained by either venipuncture or finger stick. Fluid flow through the FDS is driven by capillary forces and by thermal inkjet ("TIJ") nozzles resident on the microchip. Channel dimensions and flow path are designed to mix the blood sample with the reagent at the ideal ratio and to provide sufficient incubation time for complete erythrocyte lysis, delivering the treated sample to the microchip "just-in-time" for leukocyte analysis by impedance. One application of the device is for treatment of human whole blood samples obtained by finger stick at volumes of 10 µL or less but may also be scaled to prepare 1 to 50 microliter blood sample volumes.

Materials and Methods

Sample Delivery Component: The sample delivery component comprises the following sub-components:
 a) Reagent chamber: 6 mm diameter, 3.6 mm depth;
 b) Sample chamber: 4 mm diameter, 1.6 mm depth;
 c) Sample feed channel connecting the sample port to the mixing channel below: 0.20 mm diameter, 2.0 mm depth;
 d) Separation between the reagent and sample ports: 5 mm from edge of reagent port to center of sample port;
 e) Delivery channel dimensions: 0.32 mm wide, 0.32 mm deep, 37.0 mm long;
 f) Elastomer seal between layers; and
 g) Elastomer seal as "negative" of cup assembly.

The FDS with flex/microchip in place was inserted into the testing cassette input port and reagent was loaded into the reagent port. The reagent was allowed to wet the mixing channel and the TIJ nozzles in the microchip. A minimum 5 µL fresh human blood sample was obtained by finger stick and loaded into the sample port. The user initialed the test and obtains results using the testing cassette as directed using an automated software user interface. The blood sample was mixed with the reagent in a 1:9 ratio, flowed through the mixing channel and was delivered to the microchip with the erythrocytes completely lysed and the leukocytes intact.

Results

The device system described in this example, in concert with compatible lytic reagents, permitted automated sample preparation and 3-part WBC counting using small volumes (5 µL to 10 µL) of whole blood samples by finger stick using the microfluidic chip as described herein. This offers a significant competitive advantage over current cytology analyzers as shown in Table 1. It is noted that the superscript 1 in Table 1 refers to ABX Micros 60 CS/CT User's Manual. Horiba ABX, France. (2003), whereas superscript 2 in Table 2 Coulter® LH 750/780 Hematology Analyzer Training Module. Beckman Coulter, (2012),

TABLE 1

Contrast between results from the device described herein and pre-existing technology

|  | Example | Pre-existing Technology |
|---|---|---|
| Blood volume | 10 µL or less capillary whole blood by finger stick | 50 µL or more venous blood by venipuncture |
| Blood:lytic reagent volume ratio | 1:9 | 1:260 (WBC)[1] 1:214 (WBC)[2] |
| Number of reagents | 1 | 2 or more |
| Equipment | Microfluidic fluid delivery system and microfluidic chip on a mobile handheld point-of-care testing platform | Flow cytometer or automated hematology analyzer, non-mobile permanent laboratory appliance |
| User skills involved | Basic reading, hand dexterity, similar to use of an over-the-counter portable glucose monitor. | Formal medical technology training sufficient for CLIA certified laboratory |

As seen in Table 1, the device described herein has many benefits. Instead of needing 50 μL or more venous blood by venipuncture as in the case of pre-existing technology (e.g. Roche CoaguCheck, Abbott i-STAT®, cassettes for a range of blood glucose monitors, etc.), the device herein needs 10 μL or less capillary whole blood by finger stick. Also, in contrast to the sample-to-reagent mixing ratio in the pre-existing technology, the relative volume of the reagent needed in the device herein is at least two orders of magnitude lower. In fact, in this example, the device described herein provides an automated sample preparation system that delivers an erythrocyte-depleted, microliter-scale blood sample with leukocytes intact "just-in-time" for impedance analysis in a compatible microfluidics-based point-of-care system using TIJ technology.

The device described herein allowed for automated preparation of microliter-scale human whole blood samples obtained by finger stick to perform a 3-part WBC with % Diff., using a compatible impedance-based analyzer and reagents for continuous flow sample treatment. It allowed precise mixing of whole blood with lytic reagent at ideal ratios. It also delivered the erythrocyte depleted sample with intact leukocytes to the microchip described herein in a "just-in-time" treatment process, controlling exposure to the lytic reagent and enabling accurate lymphocyte, granulocyte, and monocyte counts by impedance sensing. Fluid flow through the device herein is controlled by capillary forces and by TIJ nozzles, enabling precise control of microliter-scale fluid volumes.

The device described herein enabled a 3-part WBC with % Diff. in a compatible analysis device at the point-of-care. It minimized, or even eliminated, the need for comparatively large volumes of blood to be drawn by venipuncture and makes possible a fundamental diagnostics blood test to occur within moments from a single drop of blood. Further, it can help improve patient care by reducing dramatically the time to results, diagnosis, and treatment and increasing access to healthcare.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The indefinite articles "a" and "an," as used herein in this disclosure, including the claims, unless clearly indicated to the contrary, should be understood to mean "at least one." Any ranges cited herein are inclusive.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A device, comprising:
   a sample delivery component, comprising:
     a reagent chamber to contain at least one reagent;
     a sample chamber to contain a biological fluid sample, the sample chamber separated from the reagent chamber by a first distance; and
     a delivery channel extending from the reagent chamber and in fluid communication with the sample chamber and an output port, the delivery channel having a length greater than the first distance, wherein the delivery channel is conducive to mixing the at least one reagent and the biological fluid sample to lyse cells in the biological fluid sample before the mixture reaches the output port and be discharged therefrom; and
   a testing cassette fitted to be compatible with the delivery component, the testing cassette comprising:
     an input port in fluid communication with a microfluidic reservoir, the input port to receive the discharged biological fluid sample from the output port; and
     a micro-fabricated integrated sensor in a microfluidic channel extending from the microfluidic reservoir.

2. The device of claim 1, wherein the micro-fabricated integrated sensor comprises an impedance-based microchip.

3. The device of claim 1, wherein the device further comprises a transport mechanism to move the biological fluid sample through the delivery channel by at least one of a capillary pump, a thermal inkjet pump, and pneumatic pump.

4. The device of claim 1, wherein the sample delivery component further comprises a sample feed channel in fluid connection between the sample chamber and the delivery channel.

5. The device of claim 1, wherein the reagent chamber comprises the at least one reagent therein.

6. The device of claim 1, wherein the testing cassette further comprises a discharge reservoir to receive the biological fluid sample that has passed through the micro-fabricated integrated sensor.

7. The device of claim 1, wherein the testing cassette further comprises at least one of:
   a membrane across a mouth of the sample input port sealing the mixture in the sample input port; and
   a removable packaging completely enclosing a body of the testing cassette body.

8. The device of claim 1, wherein the device is a part of a microfluidic diagnostic device.

9. The device of claim 1, wherein the micro-fabricated integrated sensor includes a binding surface to bind to an analyte in the biologic fluid sample.

10. The device of claim 1, wherein the testing cassette includes a resistor to mix the biologic fluid sample, and wherein the micro-fabricated integrated sensor includes an antibody binding surface made of gold to bind to an analyte in the biologic fluid sample.

11. The device of claim 1, wherein the first distance is between 1 mm and 15 mm.

12. The device of claim 1, wherein the sample chamber includes a diameter and width to accept up to approximately 20 μL of the biologic fluid sample.

13. A device, comprising:
a sample delivery component, comprising:
a reagent chamber to contain at least one reagent;
a sample chamber to contain a biological fluid sample, the sample chamber separated from the reagent chamber by a first distance;
a delivery channel extending from the reagent chamber and in fluid communication with the sample chamber and an output port, the delivery channel having a length greater than the first distance, wherein the delivery channel is conducive to mixing the at least one reagent and the biological fluid sample to lyse cells in the biological fluid sample before the mixture reaches the output port and be discharged therefrom; and
an elastomeric layer to prevent the fluid sample from leaking out of the delivery channel; and
a testing cassette fitted to be compatible with the sample delivery component, the testing cassette comprising:
a microfluidic channel;
a micro-fabricated integrated sensor in the microfluidic channel; and
a transport mechanism to pass the mixture in the microfluidic channel over a portion of the sensor for analysis.

14. The device of claim 13, wherein the transport mechanism comprises a thin film resistor, and wherein the microfluidic channel includes a flow path to provide sufficient incubation time for erythrocyte lysis of the biological fluid sample using the at least one reagent.

15. A method, comprising:
providing a biological fluid sample to a device, the device comprising:
a sample delivery component, comprising:
a reagent chamber to contain at least one reagent;
a sample chamber to contain the biological fluid sample, the sample chamber separated from the reagent chamber by a first distance; and
a delivery channel extending from the reagent chamber and in fluid communication with the sample chamber and an output port, the delivery channel having a length greater than the first distance, wherein the delivery channel is conducive to mixing the at least one reagent and the biological fluid sample to lyse cells in the biological fluid sample before the mixture reaches the output port and be discharged therefrom; and
a testing cassette fitted to be compatible with the sample delivery component, the testing cassette comprising:
an input port in fluid communication with a microfluidic reservoir, the input port to receive the discharged biologic fluid sample from the output port; and
a micro-fabricated integrated sensor within a microfluidic channel extending from the microfluidic reservoir; and
performing biologic analysis of the biologic fluid sample using at least the micro-fabricated integrated sensor.

16. The method of claim 15, wherein the micro-fabricated integrated sensor includes a binding surface having antibodies thereon, further including performing biologic analysis of the biologic fluid sample by identifying a pathogen in the biologic fluid sample that binds to the antibodies on the micro-fabricated integrated sensor.

17. The method of claim 15, including mixing in the delivery channel, the biologic fluid sample and the at least one reagent at a volume of greater than or equal to 1:100 sample to reagent.

18. The method of claim 15, wherein performing biologic analysis of the biologic fluid sample includes performing biologic analysis using a micro-fabricated integrated sensor having a binding surface to bind to an analyte, and using an impedance-based microchip.

19. The method of claim 15, including mixing the biologic fluid sample via a resistor in the testing cassette.

20. The method of claim 15, including mixing via the delivery channel, the biologic fluid sample and the at least one reagent at a volume ratio of greater than or equal to 1:200 sample to reagent.

* * * * *